United States Patent [19]
Ueda

[11] 4,106,499
[45] Aug. 15, 1978

[54] SPHYGMOMANOMETER CUFF

[75] Inventor: Kazuo Ueda, Tokyo, Japan

[73] Assignee: Ueda Works Co., Ltd., Tokyo, Japan

[21] Appl. No.: 783,524

[22] Filed: Apr. 1, 1977

Related U.S. Application Data

[63] Continuation-in-part of Ser. No. 630,466, Nov. 10, 1975, abandoned.

[51] Int. Cl.² ............................................. A61B 5/02
[52] U.S. Cl. ..................... 128/2.05 C; 128/DIG. 20; 128/327
[58] Field of Search ................... 128/2.05 C, 2.05 G, 128/327, DIG. 20

[56] References Cited

U.S. PATENT DOCUMENTS

| | | | |
|---|---|---|---|
| 1,857,567 | 5/1932 | Plesch | 128/2.05 C |
| 2,113,534 | 4/1938 | Brown | 128/327 |
| 2,320,179 | 5/1943 | Gray | 128/2.05 C |
| 3,473,525 | 10/1969 | Hanafin | 128/2.05 C |
| 3,633,567 | 1/1972 | Sarnoff | 128/2.05 C |
| 3,713,446 | 1/1973 | Sarnoff | 128/327 |
| 3,906,937 | 9/1975 | Aronson | 128/2.05 C |

FOREIGN PATENT DOCUMENTS 210,145  4/1957  Australia .................................. 128/327

Primary Examiner—Kyle L. Howell
Attorney, Agent, or Firm—William Anthony Drucker

[57] ABSTRACT

A sphygmomanometer cuff adapted to be easily applicable to any limb of a patient by himself. The cuff comprises an elongated flexible double layered fabric strap holding an inflatable pouch with tubes to be connected at the outside of the strap to a sphygmomanometer and to an air pump, and having a length sufficient to wrap by about one and a half to two turns round the patient's limb. A loop shaped rigid member is fitted at one longitudinal end of the strap, and received in the other longitudinal end thereof is a resiliently compressible rod like member. The rod like member can be forced through the loop shaped rigid member and prevents the strap from withdrawing from the loop shaped rigid member. A pair of female and male adhesive tapes are provided on the strap and are spaced apart by a distance permitting superimposing for fastening when the strap is wrapped round a patient's limb so as to stop the flow of blood through the arteries.

6 Claims, 7 Drawing Figures

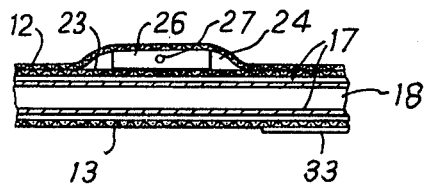
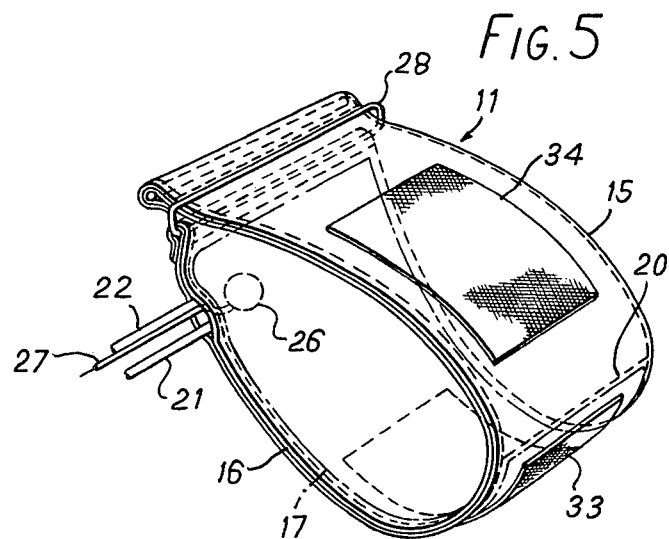
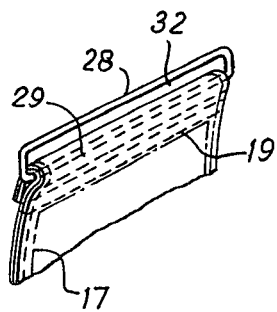
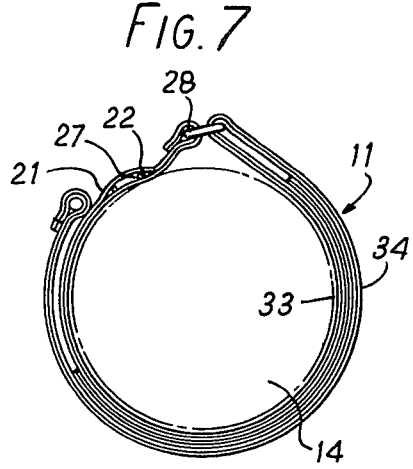

SPHYGMOMANOMETER CUFF

This is a Continuation-in-part of my co-pending U.S. Patent Application Ser. No. 630,466 filed Nov. 10, 1975, now abandoned.

BACKGROUND OF THE INVENTION

The present invention relates to a sphygmomanometer cuff (blood pressure tourniquet) adapted to apply to a limb of a person.

The prior art tourniquets were generally relatively complicated and expensive in construction, and difficult to apply to a limb of a person by himself without the aid of a helper such as a doctor or a nurse.

It is, therefore, the object of the invention to provide a sphygmomanometer cuff having an inexpensive and simple construction, and applicable as easily and quickly to a limb of a person by himself without the aid of another person.

SUMMARY OF THE INVENTION

According to the invention, there is provided a sphygmomanometer cuff comprising an elongated flexible double layered strap holding an inflatable pouch with tubes to be connected to a sphygmomanometer and to a fluid supply pump, and having a length sufficient to wrap by at least one and a half turn round a limb of a patient; a loop shaped rigid member is fitted at one longitudinal end of the strap; a resiliently compressible rod like member provided at the other longitudinal end of the strap to pass by forcing it through the loop shaped rigid member to prevent the other end of the strap from becoming disengaged from the loop shaped rigid member; and a pair of spaced fastening members, one of which is provided on one outer surface portion of the strap close to the other longitudinal end and the other of which is provided on another surface portion of the strap spaced apart from said one outer surface portion by a distance permitting superimposing for fastening to each other whenever the strap is wrapped round the patient's limb so as to stop the flow of blood through the arteries thereof.

The sphygmomanometer cuff has the advantage that it is inexpensive and simple and can easily be applied to a limb by the user himself for measuring his blood pressure without the aid of another person.

BRIEF DESCRIPTION OF THE DRAWINGS

The invention will be more fully understood from the following detailed description when taken in conjunction with the accompanying drawings, in which:

FIG. 4 is an enlarged cross sectional view of a detail taken on the line 4—4 of FIG. 2;

FIG. 5 is a perspective view of the sphygmomanometer cuff shown in FIG. 1 prior to application to a limb of a person;

FIG. 6 is a detailed perspective view of a portion of the sphygmomanometer cuff shown in FIG. 1 and including a loop shaped rigid member; and FIG. 7 is a side view of the sphygmomanometer cuff shown in FIG. 1 and applied to a limb of a person to stop the flow of blood through the arteries thereof for measuring his blood pressure.

PREFERRED EMBODIMENT OF THE INVENTION

Figure 1:
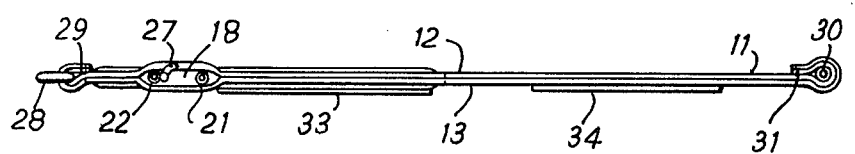
FIG. 1 is a schematic developed side elevation of a sphygmomanometer cuff in accordance with the invention.
Figure 2:
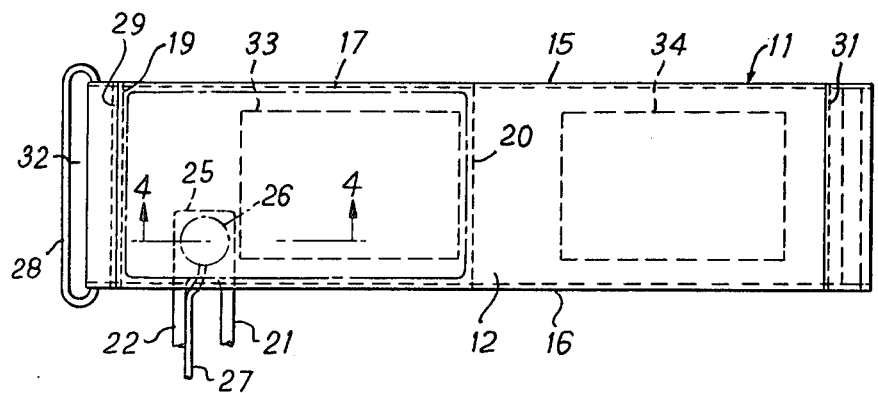
FIGS. 2 and 3 are plan and underplan views of the sphygmomanometer cuff shown in FIG. 1.
Figure 3:
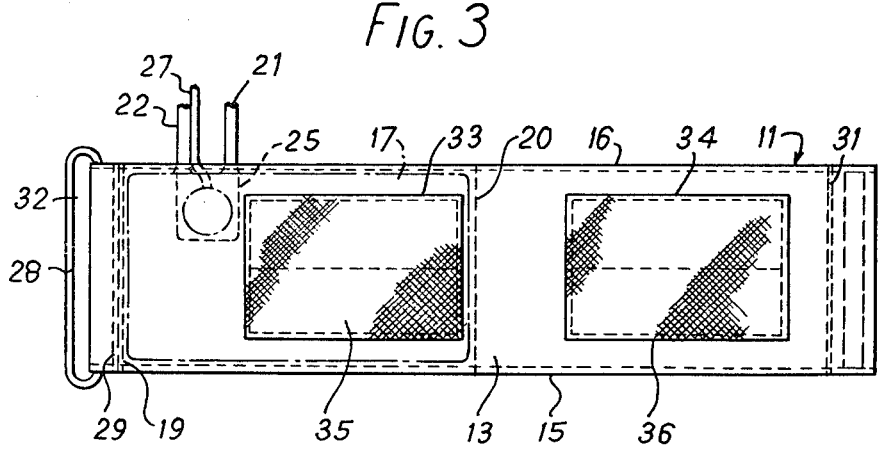

Referring now to the accompanying drawings, reference symbol 11 denotes an elongated flexible strap which is preferably made of two coextensive sheets of fabric 12 and 13 each having relatively high stiffness and a length sufficient to wrap round any desired limb 14 of any patient (see FIG. 7) by about one and a half to two turns. The fabrics 12 and 13 are superimposed and are stitched together at both longitudinal edges as shown by dotted lines 15 and 16 in FIGS. 2, 3 and 5 with an inflatable pouch or bag 17 made for example of rubber housed within a compartment 18 defined, over about half the length of the strap 11 substantially equal to one complete turn of the limb 14 of the patient whose blood pressure is to be measured, by a pair of spaced transversal lines of stitches 19 and 20, one of the lines of stitches 19 and 20 being adjacent to one longitudinal end of the strap 11 and consequently the other being positioned at about halfway along the length thereof. The inflatable pouch 17 is connected through a pipe 21 to a conventional fluid supply pump consisting preferably of a manually operated air supply pump (not shown) for inflating it, and through a pipe 22 to a sphygmomanometer (not shown). That inner surface portion of the lower fabric 12 of the strap 11 which faces a predetermined portion of the inflatable pouch 17 is superimposed with a piece of cloth 23 to form a space 24, bounded by a rectangular line of stitching 25, for holding a conventional microphone 26 as disclosed in U.S. Pat. No. 3,868,954, the microphone 26 being connected through a leadwire 27 to the microphone terminal of the sphygmomanometer.

The above-mentioned one longitudinal end of the strap 11 is either outwardly or inwardly folded to receive in the fold a portion of a loop shaped rigid member 28, for example one longer side arm of a rectangular metal ring having a length slightly longer than the width of the strap 11, and the strap end is then fixed by means of an appropriate adhesive agent or transversal line of stitching 29 to the opposite surface portion of the strap 11.

The other longitudinal end of the strap 11 is also folded with a resiliently compressible hollow or solid rod like member 30 such as rubber put within the folded wall, and is then fixed by means of an appropriate adhesive agent or transversal line of stitching 31 to the opposite surface portion of the strap 11. The rod like member 30 is formed to have its length substantially equal to the width of the strap 11 and its diameter as hereinunder described. The diameter of the rod like member 30 is selected such that the end of the strap 11 in which the rod like member 30 is received can be passed forcedly with resilient deformation through an opening or window 32 of the rectangular metal ring 28, and when it assumes its normal expanded or swelled configuration it is prevented from passing back through the window 32 of the rectangular metal ring 28.

A pair of fastening members 33 and 34 comprising, e.g. Velcro-female and male adhesive tapes are secured, in the hereinunder described relationship, to the outer surface of the upper fabric 13 of the strap 11 by means of appropriate adhesive agent or lines of stitching 35 and 36. The Velcro-female pile or adhesive tape 33 is fitted to substantially the center of one half the length of the upper fabric 13 in alignment with the inflatable pouch 17, and the Velcro-male hooked pile 34 is arranged on that portion of the other half of the length of the upper fabric 13 which does not have the inflatable pouch 17 and is spaced apart from the female pile 33 by a distance enabling the largest possible part of the male hooked pile 34 to be superimposed below the female pile 33, under the condition where the strap 11 is wrapped round the patient's limb 14 as to block the flow of blood through the arteries thereof for measuring his blood pressure (see FIG. 7).

The sphygmomanometer cuff arranged as mentioned above will be made ready for measuring the patient's blood pressure by the following steps of;

(1) passing, through the window 32 of the rectangular metal ring 28 fitted to one longitudinal end of the strap 11, the other longitudinal end thereof holding the recoverably compressible rod like member 30, with the lower and upper fabrics 12 and 13 positioned respectively inside and outside (see FIG. 5);

(2) passing the desired limb, e.g., either right or left arm through the strap 11, (3) folding back and pulling the other longitudinal end of the cuff 11 by the length or distance by which the cuff is somewhat loosely round the arm 14;

(4) fastening the female pile 33 tightly with the male hooked pile 34 as shown in FIG. 7; and (5) inflating the cuff 11 through the pipe 21 connected to the manually operated air supply pump.

As is apparent from the above description, the sphygmomanometer band of the invention has the advantage that it has an inexpensive and single construction, enabling it to be wrapped round a limb by the user easily and quickly without the aid of another person.

It should be understood to those skilled in the art that the invention is not limited only by the above-mentioned embodiment, but is applicable to its variations and modifications within the scope of the invention.

I claim:

1. A sphygmomanometer cuff comprising:
   (i) an elongated flexible strap of a length sufficient to wrap by at least one and half turns about a limb of a patient, said strap being constituted by two layers of material which, over a portion of the length of the strap are spaced apart to define an internal pocket,
   (ii) an inflatable pouch disposed in said pocket and having a first connector tube for connecting to a source of fluid under superatmospheric pressure and a second connector tube for connecting to a sphygmomanometer,
   (iii) a rigid loop-shaped member secured at a first end of the strap and defining with the strap an elongated transverse opening,
   (iv) a resiliently compressible rod-like member secured transversely at the second end of the strap, said rod-like member being adapted for forcing, with resilient deformation, through the opening defined by the loop-shaped member, said rod-like member in its unstressed condition being too thick to pass back through said opening,
   (v) a first and second cooperable fastening members, said first fastening member being secured externally on a face of said strap adjacent to said first end thereof, said second fastening member being secured externally on said face of said strap adjacent to said second end thereof, the distance between the first and second fastening members, longitudinally of the strap, and the dimensions of the first and second fastening members longitudinally of the strap, being selected such that with the strap tightened about a patient's limb, the portion of the strap terminating at its second end may be doubled over externally to superimpose the second fastening member on the first fastening member.

2. A sphygmomanometer cuff, as claimed in claim 1, wherein said strap is constituted by two coextensive sheets of fabric secured together by lines of stitching along their longitudinal edges.

3. A sphygmomanometer cuff, as claimed in claim 1, wherein said rigid loop-shaped member is a substantially rectangular metal ring including two opposed parallel longer arms and two opposed parallel shorter arms, and wherein the first end of the strap is doubled over about one of said longer arms and is secured back on itself, thereby to secure the ring to the strap with the other longer arm exposed externally of and spaced from the strap by said elongated transverse opening.

4. A sphygmomanometer cuff, as claimed in claim 1, wherein said resiliently compressible rod-like member is a hollow rubber tube, and wherein said second end of the strap is doubled over about said tube and is secured back on itself.

5. A sphygmomanometer cuff, as claimed in claim 1, wherein said first and second fastening members are respectively male and female adhesive tapes adapted for detachable engagement with each other.

6. A sphygmomanometer cuff, as claimed in claim 1, comprising a microphone disposed between said inflatable pouch and that layer of the strap which lies at the second opposed face of the strap.

* * * * *